United States Patent [19]

Chandler

[11] 4,057,997
[45] Nov. 15, 1977

[54] SAMPLE PREPARATION

[75] Inventor: Craig S. Chandler, Bartlesville, Okla.

[73] Assignee: Phillips Petroleum Company, Bartlesville, Okla.

[21] Appl. No.: 672,090

[22] Filed: Mar. 31, 1976

[51] Int. Cl.$^2$ .................... G01N 31/08; G01N 1/22
[52] U.S. Cl. ................................. 73/23.1; 73/421.5 R
[58] Field of Search ........... 73/23.1, 61.1 C, 421.5 R, 73/422 GC; 23/230, 232 C, 254 R

[56] References Cited

U.S. PATENT DOCUMENTS

| 3,236,092 | 2/1966 | Carter | 73/23.1 |
| 3,422,664 | 1/1969 | Ayers | 73/23.1 |
| 3,422,665 | 1/1969 | Haase | 73/23.1 |
| 3,508,442 | 4/1970 | Lightner et al. | 73/423 |
| 3,575,295 | 4/1971 | Yoshida et al. | 210/198 |
| 3,631,724 | 1/1972 | Oster et al. | 73/422 GC |
| 3,720,092 | 3/1973 | Reinecke | 73/23.1 |
| 3,721,253 | 3/1973 | Remke | 137/3 |

*Primary Examiner*—Jerry W. Myracle
*Assistant Examiner*—Stephen A. Kreitman

[57] ABSTRACT

In the preparation of a sample to be subjected to chromatographic separation and analysis, dilution of a sample of material to be analyzed is accomplished by combining a flow containing the sample material with a diluting flow. The diluted sample material thus obtained is sampled and analyzed. In one preferred embodiment spent carrier fluid from the chromatographic separation column can be used as the diluting stream.

23 Claims, 8 Drawing Figures

SAMPLE PREPARATION

This invention relates to preparation of a fluid sample. In another aspect the invention relates to dilution of a fluid sample. In yet another aspect the invention relates to dilution of a fluid sample for chromatographic analysis. In another aspect the invention relates to dilution of a liquid sample for liquid chromatographic analysis. In still another aspect the invention relates to a fluid sample dilution system which can utilize spent carrier fluid as a dilution solvent.

In the automatic sampling and analysis of fluids such as process fluids of a manufacturing plant, refinery, commercial chemical production system, or other similar process it is often necessary to dilute the sample of process fluid prior to subjecting the sample to analysis or otherwise using the sample for a particular desired purpose. This is particularly true when the sample is so concentrated that a controlled dilution is necessary in order to bring the sample concentration to a level which is compatible with the use to which it will be put, or when the sample is too viscous to flow through a chromatographic column, even at high pressures. Other similar problems with high viscosity of the process fluid sampled and other similar physical and/or chemical characteristics of the sampled fluid make dilution, particularly a controlled dilution in which the dilution ratio remains constant and reproducible over a long period of time during which successive samples are diluted, desirable in conjunction with many processes or production systems. In many types of sampling apparatus the smallest possible sample which can be taken is limited by physical restraints such as, for example, the minimum length of conduit used to connect the inlet and outlet ports of a sample loop in a sample valve. With the increasing sensitivity and accuracy of modern equipment such as chromatographic equipment, for example, it is often desirable to have even smaller samples of material to be analyzed since analysis of such smaller samples is well within the capability of the analyzing equipment, and use of smaller samples of material to be analyzed helps to shorten the time required for each analysis. By shortening the time required for each analysis cycle, an increased number of analysis cycles can be performed in a given time period thereby increasing the amount of work which can be done with a specified number of analyzers and/or increasing the resolution of process changes which may be reflected in the analysis of process fluids.

Accordingly, an object of the invention is to provide an apparatus and method for preparation of a fluid sample. Another object of the invention is to provide a method and apparatus for dilution of a fluid sample. Yet another object of the invention is to provide a method and apparatus for dilution of a fluid sample for chromatographic analysis. Still another object of the invention is to provide a method and apparatus for dilution of a liquid sample for liquid chromatographic analysis. Another object of the invention is to provide a fluid sample dilution system which can utilize spent carrier fluid as a dilution solvent.

In accordance with the invention a method and apparatus are provided whereby a flow of diluent fluid is established in first and second streams with a slug of sample fluid being injected into one of the streams. The first and second diluent streams are then combined to form a third stream in which the sample material contained in one of the diluent streams is combined with the diluent material in the other stream to dilute the sample material. A portion of the dilute sample material from the third stream is then removed as a diluted sample which can be used for any desired purpose. The ratio of flow between the first and second diluent streams can be established to provide the desired degree of sample material dilution. In addition, the injection of sample material into one of the diluent streams and the removal of a diluted sample from the combined stream can be accomplished in a timed relationship which is coordinated with the various flow rates of the streams to insure that a representative diluted sample is removed from the third stream. In particular preferred embodiments of the invention the dilution system can be utilized in conjunction with a method and apparatus for providing chromatographic separation of the constituents within the diluted sample. When such a chromatographic separation or analysis is to be performed on the diluted sample, the chormatographic carrier fluid can be utilized as the diluent and, in a particularly preferred embodiment, the spent chromatographic carrier fluid discharged from the chromatographic separation column can be utilized as the source of diluent fluid for the first and second diluent streams.

Other objects and advantages of the invention will be apparent from the specification of the invention and the appended claims thereto as well as from the detailed description of the drawing in which

Figure 1:
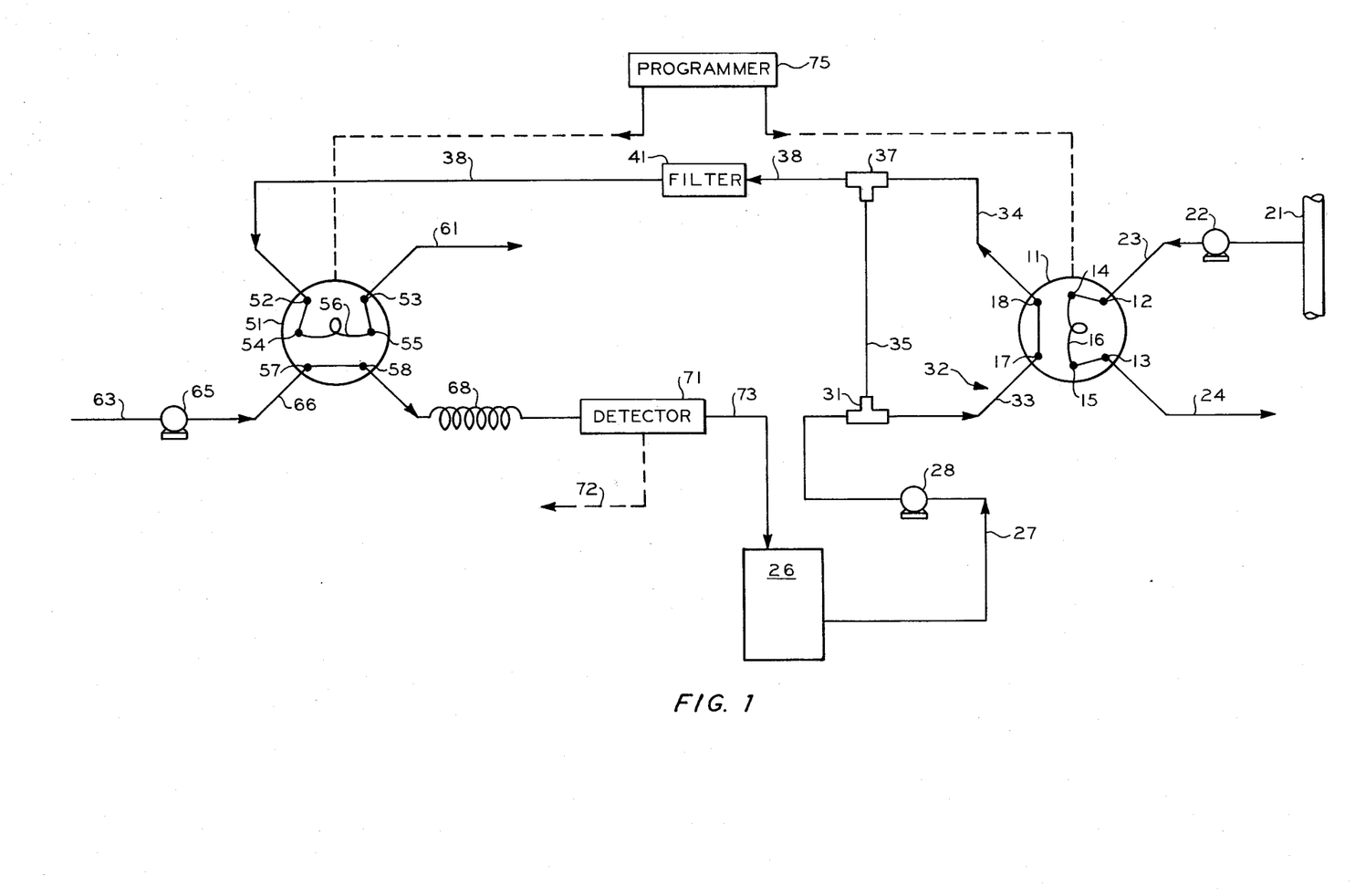
FIG. 1 is a schematic representation of a chromatographic analysis apparatus utilizing the dilution apparatus of the invention and employing spent carrier fluid as a dilution fluid.

Referring to FIG. 1, there is illustrated a first sample valve 11 having a sample inlet port 12, a sample outlet port 13, sample loop ports 14 and 15 having a sample loop means 16 connected therebetween, a dilution fluid inlet port 17 and a dilution fluid outlet port 18.

A process conduit 21 or other suitable source of process fluid to be diluted is suitably connected in fluid communication through a pump means 22 or other similar source of fluid flow impetus to a sample inlet conduit 23 operably connected to the sample inlet port 12 of the first valve 11. A sample outlet conduit 24 is connected to the sample outlet port 13 of the first valve 11. The sample outlet conduit 24 can be operably connected to any suitable means for disposing of the unused sample material passing through the sample valve 11, including process conduit 21, other process conduits or vessels, or other suitable disposal means.

Figure 2:
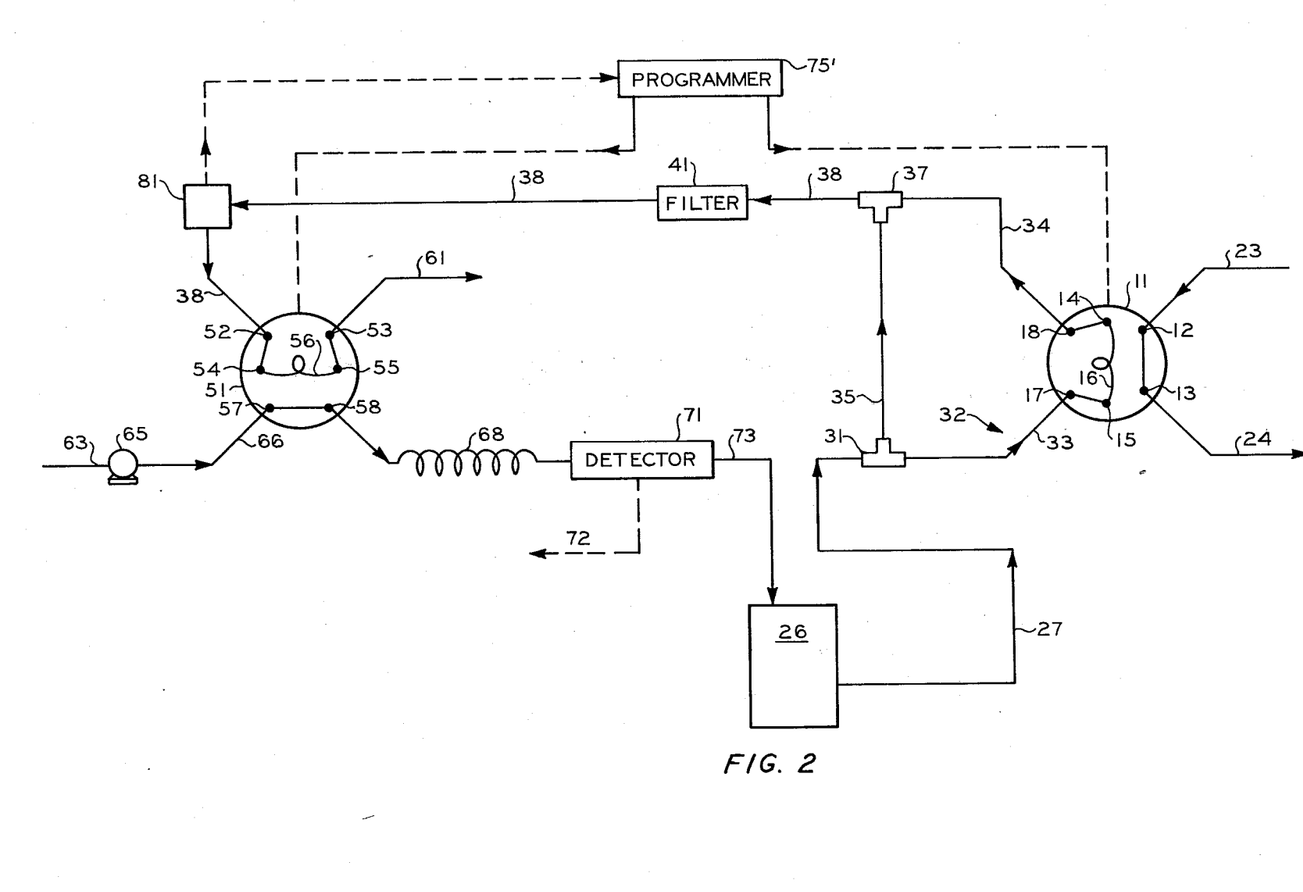
FIG. 2 is a schematic representation of a modified version of the apparatus of FIG. 1.

A diluent fluid reservoir 26 containing a supply of a suitable diluent fluid is connected in operable fluid communication with a diluent supply conduit means 27 which is, in turn, in operable fluid communication with a tee means 31. The diluent supply conduit 27 may have associated therewith a pump means 28 or other suitable means for providing adequate fluid pressure to insure the desired flow of diluent fluid to the tee means 31. The tee means 31 divides the flow of diluent fluid from the supply conduit means 27 into a first diluent stream entering the upstream portion 33 of a first diluent stream conduit means 32 and a second diluent stream entering a second diluent conduit means 35. Connection of the upstream portion 33 of the first diluent conduit 32 to the diluent inlet port 17 of the first sample valve 11 and connection of the diluent outlet port 18 of the sample valve 11 to the downstream portion 34 of the first diluent conduit 32 operatively incorporates the first sample valve 11 into the first diluent conduit 32. When the first sample valve 11 is in a first position as illustrated by FIG. 1, the upstream portion 33 and downstream portion 34 of the first diluent conduit 32 are connected by communication within the valve 11 being established directly between ports 17 and 18. When the valve 11 is switched to its second position (as illustrated by FIG. 2), the sample loop 16 is interposed between the upstream portion 33 and downstream portion 34 of the first diluent conduit 32, thereby injecting the contents of the sample loop 16 into the first diluent stream flowing through the first diluent conduit 32.

A second tee means 37 provides for fluid communication between the downstream portion 34 of the first diluent conduit 32 and the downstream portion of the second diluent conduit 35, thereby combining the first and second diluent streams as a third diluent stream in a third diluent conduit means 38. The third diluent conduit means 38 may contain such additional equipment as may be appropriate for properly preparing the diluted sample material flowing therethrough. A filter means 41, for example, may be utilized with apparatus in which a liquid sample material which may contain insoluble particulate material in order to prevent introduction of such particulate material into a chromatographic column or other similar apparatus to which a portion of the diluted sample may be provided.

A second sample valve means 51 has associated therewith a sample inlet port 52, a sample outlet port 53, sample loop ports 54 and 55 operably connected in fluid communication with opposite ends of a sample loop 56, a carrier inlet port 57, and a carrier outlet port 58. The general operation of the second sample valve 51 is similar to that of the first sample valve 11 in that placing the valve in a first position, illustrated by FIG. 1, interposes the sample loop 56 between the sample inlet port 52 and the sample outlet port 53 and provides direct communication between the carrier inlet port 57 and the carrier outlet port 58. In the valve's second position (illustrated by FIG. 3), direct fluid communication is provided between the sample inlet port 52 and the sample outlet port 53, and the sample loop 56 is interposed between the carrier inlet port 57 and carrier outlet port 58 in order to inject the material contained in the sample loop 56 into the stream of fluid flowing into the carrier inlet port 57 of the second sample valve 51.

The third diluent conduit 38 is connected in fluid communication with the sample inlet port 52 in order to provide diluted sample material thereto. A diluent disposal conduit 61 is connected in fluid communication with the diluent outlet port 53 in order to provide for disposal or other use of diluent fluid and diluted sample material which is not injected into the carrier stream by the second sample valve means 51.

A carrier supply conduit 63 provides a supply of a suitable chromatographic carrier fluid to a pump means 65 which in turn delivers a carrier fluid stream under suitable pressure to a carrier inlet conduit 66. The carrier inlet conduit 66 is in operable fluid communication with the carrier inlet port 57 of the second sample valve 51. The carrier outlet port 58 of the valve 51 is connected in operable fluid communication with the inlet of a chromatographic separation column 68. Fluid exiting the chromatographic separation column 68 is delivered to a chromatographic detector means 71 which produces, in response to the content of the fluid passing therethrough, a chromatographic analysis signal 72 representative of the relative concentrations of various constituents eluted through the chromatographic separation column 68.

In the preferred embodiment illustrated, the diluent fluid and chromatographic carrier fluid are of substantially the same composition, as the effluent from the chromatographic detector means 71 is delivered to the diluent fluid reservoir 26 by a chormatographic effluent conduit 73. Although the effluent from the chromatographic detector means 71 will contain, in addition to the fluid used as a carrier and diluent, the sample material which has been injected into the carrier stream for analysis, the use of a relatively large diluent fluid supply vessel 26 in which the diluent fluid and any sample material contained therein are thoroughly mixed prior to withdrawal of diluent material for use in sample dilution will permit operation of the illustrated apparatus without interference from residual process fluid sample constituents. Two main characteristics of the system make such operation possible. First, the dilution of the original sample and passage of only a small portion of the original sample to the chromatographic analysis apparatus, coupled with the fact that the volume of carrier fluid passing through the chromatographic separation column 68 during the separation of a sample is substantially greater than the sample fluid volume, will cause the concentration of sample material within the diluent fluid reservoir 26 to be so small that little if any interference with a sample being analyzed will result. Secondly, even if the concentration of sample material within the diluent reservoir 26 is high enough to be detectable by the chromatographic analysis apparatus, thorough mixing within the diluent reservoir 26 along with continuing operation using relatively constant carrier flow rates and analysis cycle times will cause the fluid material within the diluent reservoir 26 to be maintained at a substantially constant composition thereby removing the presence of sample constituents within the diluent fluid as a variable of the analysis system.

A programmer means 75 can be operably connected to the first sample valve means 11 and to the second sample valve means 51 in order to cause operation of the sample valves in a timed relationship so that injection of a diluted sample from the sample loop 56 into the carrier stream entering the chormatographic separation column 68 is accomplished during the time that a representative diluted sample is present within the sample loop 56 following injection of the process liquid sample from the sample loop 16 into the first diluent conduit 32. Although the programmer 75 can operate in response to a detector signal or other similar signal, in the preferred embodiment illustrated the programmer 75 operates by actuating the second sample valve means 51 at a fixed time following actuation of the first sample valve means 11. The time between actuation of the two valves is preferably determined by selecting a time at which, with the flow rates of the first and second diluent stream being maintained at a constant level, a representative diluted sample will be present within the sample loop 56 of the second sample valve 51.

FIG. 2 illustrates apparatus similar to that of FIG. 1 utilizing recirculation of expended carrier fluid as a diluent stream and, in addition, utilizing a single source of fluid pressure, pump means 65, as a source of pressure for both the carrier fluid stream and the diluent fluid streams. In addition, the apparatus includes a detector 81 which can be utilized to sense the presence of the diluted sample at the second sample valve means 51 and cause the programmer 75' to initiate actuation of the second sample valve 51 when a representative diluted fluid sample can be injected into the carrier stream. Although the embodiment of FIG. 2 is illustrated using a diluent storage vessel 26, it is possible, by using additional timing restraints imposed by the programmer 75' on the operation of the first sample valve 11 and second sample valve 51, to provide fluid communication directly between conduits 73 and 27. When this configuration is used, injection of a sample by the sample valve 11 into the first diluent stream flowing through the first diluent conduit 32 is avoided when the material from a previously injected sample would interfere with the dilution of a new sample. The remains of previously injected samples are permitted to recirculate through the first and second diluent conduits and the third diluent conduit 38 and exit the system through the disposal conduit 61 associated with the second sample valve 51. The disposal of sample constituents which have been eluted through the chromatographic separation column 68 is therefore accomplished in the same manner as the disposal of diluted sample constituents which are not injected into the carrier stream by the second sample valve 51.

Figure 3:
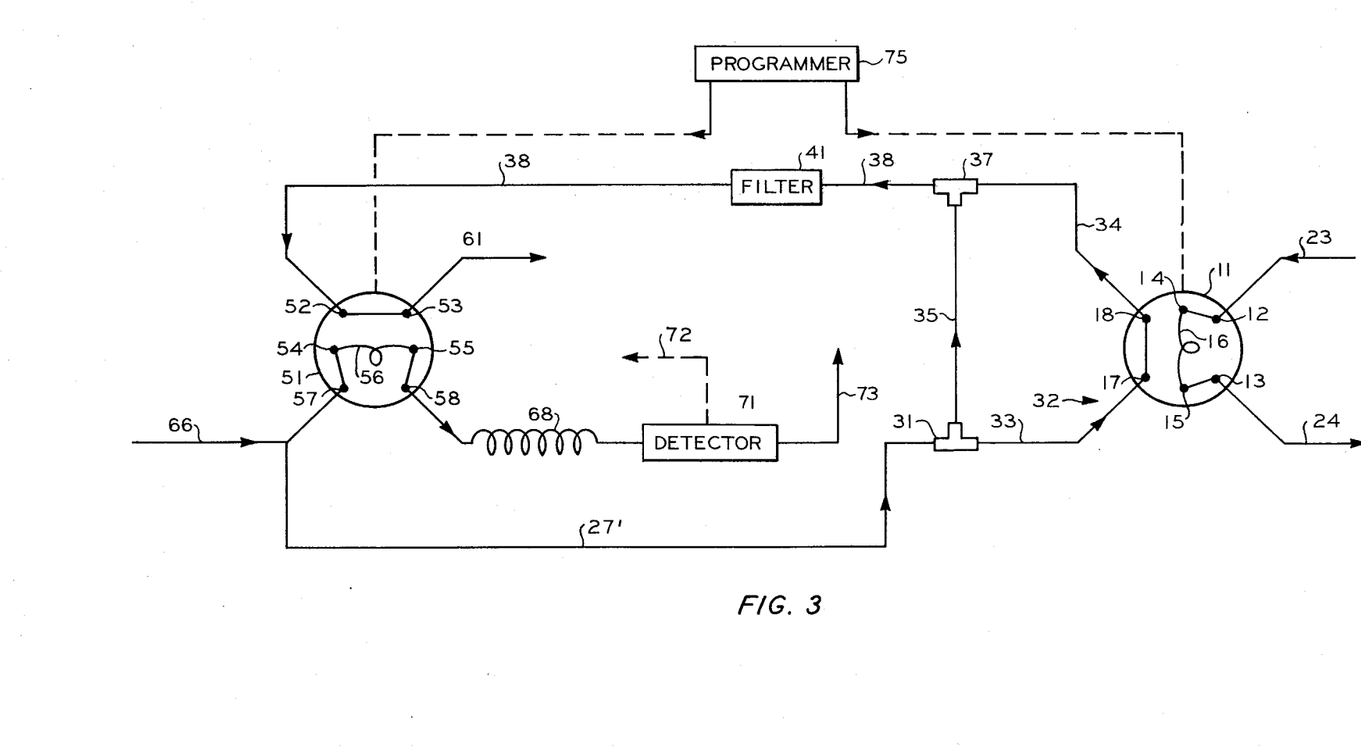
FIG. 3 is a schematic representation of a chromatographic analysis apparatus employing the dilution apparatus of the invention and utilizing fresh chromatographic carrier fluid as a dilution fluid.

FIG. 3 illustrates chromatographic analysis apparatus utilizing the apparatus and method of the invention and illustrates the apparatus of FIG. 1 adapted to utilize the carrier inlet conduit 66 as the source of dilution fluid by providing suitable fluid communication between the conduit 66 and a dilution fluid inlet conduit 27'. In other respects, the apparatus illustrated by FIG. 3 operates in the same manner as the apparatus of FIG. 1. In the apparatus of FIG. 3 the effluent from the detector 71 exiting the detector 71 through conduit 73 is disposed of by any suitable means rather than being reused or recirculated. The apparatus of FIG. 3 is particularly useful as an alternative to the apparatus illustrated by FIG. 1 when some characteristic of either the carrier and diluent fluid or the sample material makes it undesirable to recirculate the effluent from the detector 71 through the system using either a diluent reservoir 26 as illustrated in FIGS. 1 and 2 or a direct connection between the detector effluent conduit 73 and the diluent inlet conduit 27 or 27'.

Using apparatus of the type illustrated by FIGS. 1–3, dilution ratios of total fluid to sample within a range of from about 1:200 to about 200:1 are possible and dilution ratios of from about 1:10 to about 10:1 can easily be obtained. In general, the majority of process applications will require a dilution ratio of total fluid to sample within the range of from about 1:1 to about 10:1. To obtain a desired ratio, a careful selection of the piping or tubing used is necessary with particular attention directed to the relative size and length of the first diluent conduit 32 and the second diluent conduit 35. Choice of conduit size and flow characteristics rather than use of valves is preferred for obtaining a desired dilution ration in order to avoid the possibility of undesired opening or closing of mechanical valves causing unwanted change in the sample dilution ratio. Where the flow rate through the first diluent conduit means 32 is designated as $F_1$ and the flow rate through the second diluent conduit means 35 is designated as $F_2$, the total flow through both the first and second diluent conduits will be $F_t$ where $$F_t = F_1 + F_2.$$

With a preferred diluent to sample ratio of from about 1:1 to about 10:1 wherein $F_2 \geqq F_1$, the dilution of the dilute sample falling from the tee 37 into the third diluent conduit 38 can be expressed as $$\text{Dilution} = F_t/F_1.$$

The actual tubing or conduit size to be used can vary greatly. In many modern chromatographic analysis systems, for example, the desire for rapid analysis of a sample has led to the use of extremely small conduit sizes in order to maintain a high rate of flow through the analysis system and to thereby decrease the length of time required to move a sample to a chromatographic separation column or other similar analysis apparatus. The desire to use extremely small sample volumes, some as small as two microliters for example, has also resulted in use of extremely small inside diameter conduit. The method and apparatus of the invention can be permitted using conduits ranging in size from capillary sized inside diameters which need be only large enough to provide a desired flow therethrough up through standard 1/16-inch, ⅛-inch, and larger tubing. Both the size and the length of various portions of the apparatus conduit can be selected to provide desired flow rates and flow ratios in each portion of the apparatus.

Although dilution far in excess of 10:1 can be achieved in accordance with the invention, greater dilutions obviously carry with them a slower relative flow rate through the first diluent conduit conduit means 32 as well as a spreading of the diluted sample over a greater distance within the third diluent conduit 38. Under these conditions a greater length of time is required for taking each sample of process fluid from its point of injection into the first diluent conduit means 32, through the third diluent conduit means 38 and from the system either as a diluted sample injected into the carrier stream by the second sample valve 51 or as excess diluted sample removed from the system through the discharge conduit 61 associated with the second sample valve 51. The minimum time between successive analysis cycles is thereby increased. Such an increase in sampling intervals will, in many applications, prohibit operation of the analysis apparatus at its maximum successive analysis cycle rate. In order to achieve such high dilutions and still maintain a desirably short analysis cycle rate, the apparatus of the invention, such as the apparatus illustrated by FIG. 3, can be modified as illustrated by FIG. 4 to provide bypassing of those flow restrictions which are the primary cause of delay in readying the apparatus to receive another sample of process fluid and providing for fluid flow through bypass means to clear excess sample material from the system after a representative sample of the diluted material has been injected into the carrier stream for chromatographic analysis.

Figure 4:
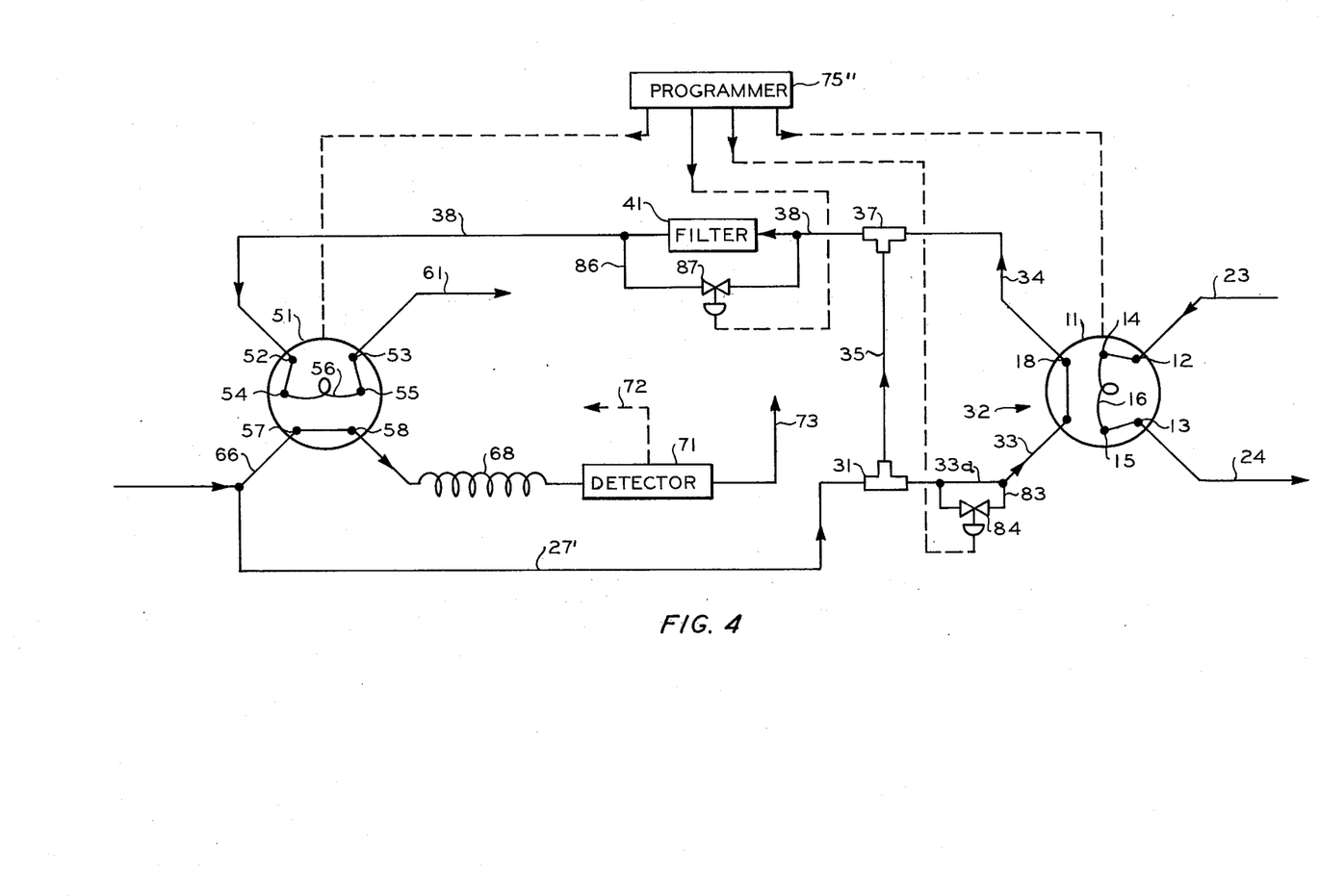
FIG. 4 is a schematic representation of a modified version of the apparatus of FIG. 3.

In the apparatus illustrated by FIG. 4, the upstream portion 33 of the first diluent conduit 32 contains a length of flow restrictive conduit 33a which, along with the size of the second diluent conduit 35, is primarily determinative of the ratio of flow between the first diluent conduit 32 and the second diluent conduit 35. A bypass conduit means 83 containing a suitable valve means 84 bypasses the flow restriction 33a of the upstream portion 33 in the first diluent conduit 32. In a similar manner, a bypass conduit 86 containing a suitable valve means 87 bypasses the filter means 41 in the third diluent conduit 38. The programmer 75" controls valves 84 and 87 as well as the first sample valve means 11 and the second sample valve means 51. The operation of all other portions of the apparatus of FIG. 4 is as described in conjunction with the detailed description of FIGS. 1–3.

In the analysis of a sample by the system of FIG. 4, valve means 84 and 87 are initially closed and carrier flow is established through the chromatographic detection apparatus as well as through the dilution apparatus of the invention. At a suitable time determined by the programmer 75", the sample within the sample loop 16 of the first sample valve 11 is injected into the first diluent stream 32 downstream of the flow restriction 33a thereof. The injected sample material is carried through the downstream portion 34 of the first diluent stream 32 to the tee 37 where it is combined with the flow of diluent material through the second diluent stream 35 and thereby diluted as it enters the third diluent stream 38. The diluted sample flows through the filter means 41 located within the third diluent conduit 38 and, when sufficient time has elapsed for a representative portion of the diluted sample material to be within the sample loop 56 of the second sample valve means 51, the programmer 75" actuates the second sample valve 51 to inject the portion of the diluted sample material within the sample loop 56 into the carrier stream flowing into the chromatographic separation column 68. As soon as injection of a portion of the diluted sample material into the stream flowing through the chromatographic separation column is complete, the programmer 75" can be utilized to open valves 84 and 87, thereby permitting flow around the restriction 33a and filter 41. The resulting increased flow rate to the downstream portion 34 of the first diluent conduit 32 and through the third diluent conduit 38 will remove remaining diluted and undiluted sample material from those conduits more rapidly than if continued operation without utilizing bypass conduits 83 and 86, and the system can be more quickly readied to accept a subsequent injection of process fluid sample material. Prior to injection of a subsequent process material sample, valves 84 and 87 will be closed in response to signals from the programmer 75". At the time valve 87 is reclosed, any diluted sample material which may have been remaining within the filter 41 at the time the valve 87 was opened and which may not have been removed from the filter 41 by parallel flow therethrough during the time which the bypass conduit 86 was in use, will be removed from the filter means 41 and carried from the discharge conduit 61 prior to the arrival at the second sample valve means 51 of the diluted portion of any subsequent sample.

Figure 5:
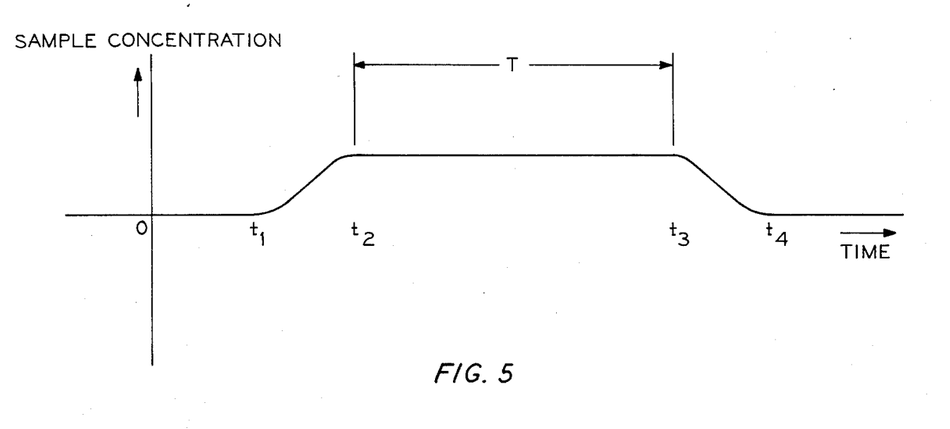
FIG. 5 is a graphical representation of the sample concentration within the combined diluent fluid stream of the invention.

FIG. 5 is a graphical representation of the relative concentration of sample material at any preselected point in the third diluent conduit 38 such as, for example, the point at which the third diluent conduit 38 is connected in fluid communication with the sample inlet port 52 of the second sample valve means 51. The graphical representation illustrated by FIG. 5 would likewise be representative of response which could be expected from the output of the detector 81 of FIG. 2. The relative time duration of various portions of the curve will obviously vary from one application to another depending on the flow rates and conduit lengths involved. At a time designated in FIG. 5 as time zero when injection of a sample of process fluid material into the first diluent stream is accomplished, the sample concentration within the third diluent conduit 38 at or near the second sample valve means 51 has been assumed to be substantially zero as illustrated. Although this will ordinarily be the case in many specific applications, injection of a subsequent sample prior to removal of all diluted sample from the third diluent conduit can be used to shorten the analysis cycle time of the system without sacrificing the accuracy of the dilution or diluted sample composition. At some subsequent time $t_1$ sample material will begin to arrive at the second sample valve 51. During a relatively short period of time from $t_1$ to $t_2$ the concentration of sample constituents within the third diluent stream increases from substantially zero to a substantially constant level which has been determined by the relative rates of flow through the first diluent conduit means 32 and the second diluent conduit means 35. The exact length of the time from $t_1$ to $t_2$ in any specific application will depend on the velocity of flow through the various conduits involved, the amount of mixing which may take place within the filter 41 or within any of the conduits involved, spreading or mixing effects which may take place at the leading edge of the sample when the sample material from a process is inserted into the first diluent stream, and other similar causes.

From time $t_2$ to $t_3$, a time interval represented in FIG. 5 as T, the concentration of sample material arriving at the second sample valve 51 is maintained at a value determined by the dilution ratio established as the first and second diluent streams were combined in the tee means 37. When the graph of FIG. 5 is representative of the sample concentration within the sample loop 56, injection of the contents of the sample loop 56 associated with the second sample valve means 51 into the carrier stream at the entrance of the chromatographic separation column 68 at a time during the period T and within the time range of $t_2$ to $t_3$ by the programmer 75, 75', or 75" will result in an accurately representative portion of the diluted sample material being selected for chromatographic separation and analysis. From time $t_3$ to $t_4$ the trailing edge of the diluted sample passes through the sample loop 56. During the time following $t_4$ the concentration of sample material within the sample loop 56 is again substantially zero.

When successive samples are to be analyzed as rapidly as possible, injections of subsequent sample material into the first diluent stream can be accomplished as rapidly as is desirable, as long as the sample is not interfered with by remnants of a preceding sample within the dilution system. In order to minimize demands on the programmer 75, 75', or 75" employed as well as demands on the instrumentation which is used to process the analysis signal 72 and to perform control functions in reponse thereto, it is normally desirable to complete analysis of one sample prior to injecting another sample into the system so that all events associated with the analysis of a particular sample will be accomplished within one single sequential cycle. The use of overlapping cycles wherein a subsequent sample is injected into the system prior to completion of analysis of the previous sample can, however, be accomplished using the apparatus and method of the invention at the cost of some increase in complexity of the programmer or other control apparatus involved.

Operation in accordance with the invention can use a fluid other than the carrier fluid as a diluent by connecting the appropriate conduit 27 or 27' to a suitable source of other diluent fluid. Use of the carrier fluid as the diluent is preferred in those cases where such use is feasible since the necessity for providing a separate diluent fluid supply is thereby avoided.

In the choice of particular equipment which is to be incorporated into the apparatus of the invention, it is preferred that the tee means 37 have the same approximate effective inside diameter as the downstream portion 34 of the first diluent conduit means 32 and the second diluent conduit means 35. Although a tee means 37 having a differing size can be used in the practice of the invention, the relative length of time between times $t_1$ and $t_2$ in FIG. 5 should ordinarily be minimized by the use of a tee means 37 having an inside diameter which is not substantially greater than the inside diameter of those conduits with which it connects. The use of a tee means 37 having an inside diameter substantially smaller than the conduits 34 and 35 should not deleteriously affect the tendency of the diluted sample to spread but could make it more difficult to size upstream conduits to properly achieve a desired flow and dilution ratio.

The method and apparatus of the invention are particularly useful in the dilution of a liquid sample such as a carbon black feedstock oil or other heavy oil. Because of the size of the smallest samples which can be obtained with commonly used instruments is limited, the sample volume must be diluted to keep the output signal from the chromatographic detector 71 on scale, especially when the detector used is an ultraviolet detector or other similarly sensitive detector means. Since the method and apparatus of the invention provide constant and reproducible dilution of the original sample, the exact amount of dilution of the original sample in a given system can readily be determined and, knowing the amount of dilution, the concentration of the components in the original sample can be calculated or even programmed into the analysis apparatus by means of a scaling factor applied to the detector output signal 72, or by other similar suitable means.

EXAMPLE

Apparatus corresponding generally to the apparatus schematically illustrated by FIG. 3 was constructed utilizing, as the first sample valve 11, a Model VIII high pressure liquid chromatographic sample valve, available from Applied Automation, Inc., Bartlesville, Oklahoma, having an external sample loop of one-sixteenth inch tubing having a volume of approximately 1 cubic centimeter. This relatively large sample loop provided an excess of sample material with the amount of sample material actually introduced into the dilution system being controlled by the length of time the first sample valve 11 was maintained with its sample loop in the first conduit means 32. The second sample valve 51 utilized was also a Model VIII high pressure liquid chromatographic sample valve and had a 2 microliter internal sample loop. Operation of the sample valves was controlled by a Model 102P programmer manufactured by Applied Automation, Inc., Bartlesville, Oklahoma. The chromatographic analysis apparatus utilized was an Optichrom LC analyzer manufactured by Applied Automation, Inc., Bartlesville, Oklahoma in which the chromatographic separation column 68 comprised three separate columns connected in series and totaling 6 inches in length, each column having an inside diameter of about 0.180 inches (4.6 mm), and each column being packed with 5 micron LiChrosorb packing material available from Applied Research Laboratories, 9545 Wentworth, Sunland, Calif. 91040. Normal hexane was used as both the carrier fluid for the chromatographic analyzer and the diluent for the sample. Carrier flow through the chromatographic column was maintained at approximately 2 cubic centimeters per minute with carrier through the reference cell of the ultraviolet chromatographic detector maintained at about 1 cubic centimeter per minute. The normal hexane carrier was supplied to the second valve 51 at a pressure of approximately 1000 psi (6900 kPa). The normal hexane diluent was supplied through a separate supply system to the first and second diluent streams at a pressure of about 50 psi (345 kPa). The first sample valve 11, first diluent conduit means 32 and second diluent conduit means 35 were located in a heated enclosure maintained at approximately 150° F. (65° C). The upstream portion 33 of the first diluent conduit means 32 comprised an 8 ft. (2.44m) length of 0.005 inch (0.13 mm) inside diameter tubing providing a flow of about 0.0375 cubic centimeters per minute therethrough. The second diluent conduit means 35 comprised a length of 0.010 inch (0.25 mm) inside diameter tubing sufficient to provide a flow of about 5.75 cubic centimeters per minute therethrough, thereby providing a dilution of about 154:1.

The third diluent conduit 38, second sample valve 51, and chromatographic analysis apparatus were located at a separate enclosure maintained at approximately 75° F. (22° C.). The third diluent conduit means 38 did not contain a filter.

In order to establish representative information relative to the accuracy of the second sample valve means 51, a control sample solution comprising benzene diluted in normal hexane at a dilution ratio of about 200:1 was prepared by hand and supplied to the inlet port 52 of the second sample valve 51 for automatic sampling by the sample valve and introduction into the chromatographic detection apparatus. The reproducibility of such sampling and analysis of the known diluted control sample is illustrated by the chromatogram of FIG. 6 wherein each peak represents the bezene content of a separate successive sampled portion of the diluted control sample.

Figure 7:
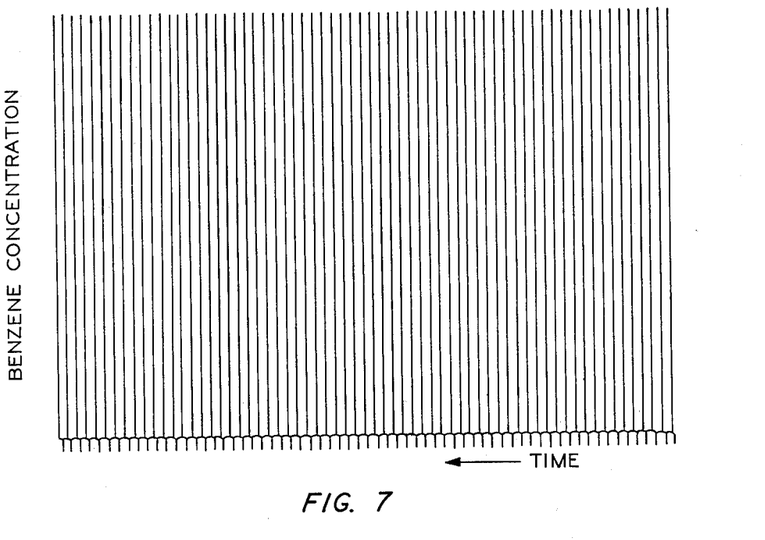
FIGS. 7 and 8 are chromatographic analyzer outputs illustrating the accuracy and reproducibility of the dilution system of the invention in conjunction with a chromatographic sampling system.
Figure 8:
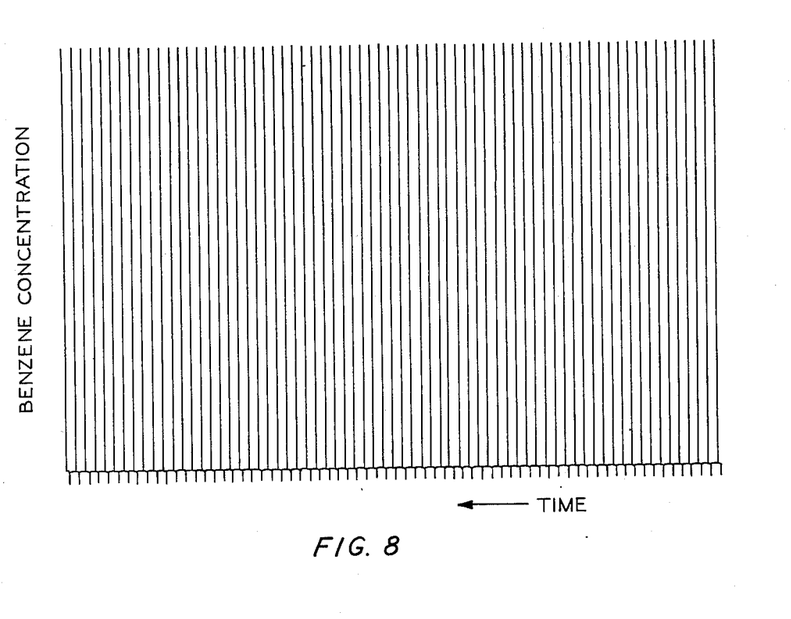

Following establishment of the operating characteristics of the second sample valve means 51 and the chromatographic analysis apparatus, a flow of benzene was supplied to the sample loop 16 on the first sampling valve 11. Automatic sampling of the bezene supply was initiated at about 3½ minute intervals with the programmer controlling both the operation of the first sample valve means 11 and the subsequent operation of the second valve means 51. The sample loop 16 was maintained in the first diluent conduit means 32 for a period equal to about two-thirds of the sample interval time. Operation of the second sample valve means 51 was timed to permit the diluted flow of benzene through the sample loop 56 of the second sample valve means 51 to reach a constant representative value prior to injection of the diluted sample into the chromatographic analysis apparatus. FIG. 7 is a chromatogram illustrating the reproducibility of the sample apparatus and method at the beginning of the test run. FIG. 8 is a chromatogram corresponding to the chromatogram of FIG. 7 but taken after 7 days of continuous operation of the dilution and analysis apparatus.

Figure 6:
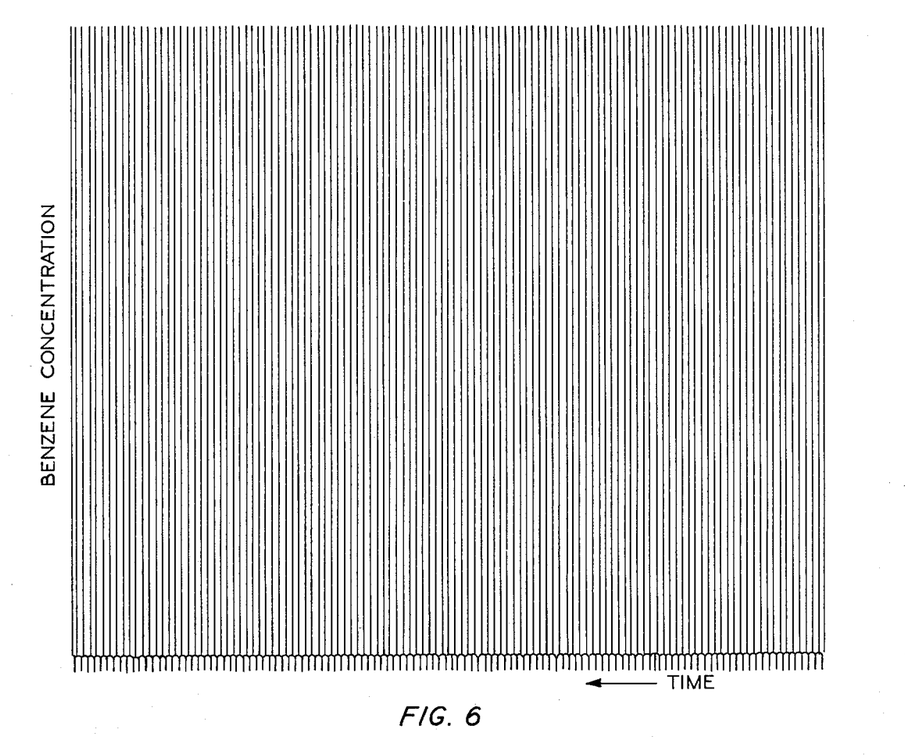
FIG. 6 is a chromatographic analyzer output illustrating the accuracy and reproducibility of standard sampling equipment.

A comparison of FIGS. 6, 7, and 8 illustrates that the dilution system of the invention is as accurate as the precision chromatographic valves and analysis equipment with which it was tested and that the dilution system of the invention is capable of maintaining its consistently reliable accuracy over a period of sustained operation.

Although a sample loop 16 having a volume chosen to permit complete employing of the loop by first diluent stream flow during an analysis cycle, the technique of using a sample loop 16 having excess capacity is also acceptable with timing of sample valve operation being used to determine the actual amount of sample injected. Using this latter technique, the time which the sample loop 16 remains a part of the first diluent conduit will correspond generally to the time during which a representative diluted sample is available at the second sample valve 51 when all flow rates remain substantially constant.

Although the invention has been described herein in conjunction with the preferred embodiment thereof, reasonable variations and modifications within the scope of the invention and of the appended claims thereto are within the capability of those skilled in the art.

I claim:

1. Apparatus comprising:
    fluid sample material supply means for providing a supply of fluid sample material;
    first, second, and third diluent conduit means for providing respective first, second, and third diluent fluid paths, each said diluent conduit means having an upstream end and a downstream end;
    diluent material supply means for providing a flow of diluent material to the upstream ends of said first and second diluent conduit means;
    first tee means for providing fluid communication among the downstream end of said first diluent conduit means, the downstream end of said second diluent conduit means, and the upstream end of said third diluent conduit means;
    means for injecting a preselected volume of sample material from said sample material supply means into said first diluent conduit means at a location intermediate of the upstream and downstream ends of said first diluent conduit means; and
    means for removing a preselected volume of material from said third diluent conduit means to provide a diluted sample.

2. Apparatus in accordance with claim 1 wherein said diluent material supply means comprises:
    diluent reservoir means for maintaining a supply of diluent fluid therein;
    diluent supply conduit means for providing a flow of diluent material therethrough, said diluent supply conduit means having an upstream end and a downstream end, said upstream end thereof being in fluid communication with said diluent reservoir means; and
    second tee means for providing fluid communication among the upstream end of said first diluent conduit means, the upstream end of said second diluent conduit means, and the downstream end of said diluent supply conduit means.

3. Apparatus in accordance with claim 1 additionally comprising a chromatographic separation apparatus, wherein said means for removing a preselected volume of material from said third diluent conduit comprises means for injecting said preselected volume of material from said third diluent conduit into a carrier fluid stream of a chromatographic separation apparatus.

4. Apparatus in accordance with claim 3 wherein said chromatographic separation apparatus comprises an analyzer effluent conduit means for discharging carrier and sample material eluted through said chromatographic separation apparatus, and wherein said analyzer effluent conduit means is in fluid communication with said diluent material supply means.

5. Apparatus in accordance with claim 4 wherein said diluent material supply means comprises:
    diluent reservoir means for maintaining a supply of diluent fluid therein;
    diluent supply conduit means for providing a flow of diluent material therethrough, said diluent supply conduit means having an upstream end and a downstream end, said upstream end thereof being in fluid communication with said diluent reservoir means; and
    second tee means for providing fluid communication among the upstream end of said first diluent conduit means, the upstream end of said second diluent conduit means, and the downstream end of said diluent supply conduit means.

6. Apparatus in accordance with claim 5 wherein said diluent supply conduit means comprises pump means for providing flow impetus through said diluent supply conduit means.

7. Apparatus in accordance with claim 4 wherein said means for removing a preselected volume of material from said third diluent conduit comprises a sample valve means operatively connected in said third diluent conduit, means operatively associated with said third diluent conduit at a predetermined location upstream of said sample valve to detect the presence of said sample material in said third conduit at said predetermined location, and means responsive to said means to detect to operate said sample valve means in predetermined time relationship with the detection of sample material at said predetermined location.

8. Apparatus in accordance with claim 4 further comprising means for increasing the flow rate of fluid in said first diluent conduit means after the removal of said preselected volume of material from said third diluent conduit means.

9. Apparatus in accordance with claim 1 wherein said means for removing a preselected volume of material from said third diluent conduit comprises a sample valve means operatively connected in said third diluent conduit, means operatively associated with said third diluent conduit at a predetermined location upstream of said sample valve to detect the presence of said sample material in said third conduit at said predetermined location, and means responsive to said means to detect to operate said sample valve means in predetermined time relationship with the detection of sample material at said predetermined location.

10. Apparatus in accordance with claim 1 further comprising means for increasing the flow rate of fluid in said first diluent conduit means after the removal of said preselected volume of material from said third diluent conduit means.

11. A sampling method comprising:
establishing a first diluent stream having a flow of a diluent fluid passing therethrough at a first flow rate;
establishing a second diluent stream having a flow of said diluent fluid passing therethrough at a second flow rate, said second flow rate bearing a fixed relationship to said first flow rate;
injecting a preselected volume of sample material into said first diluent stream;
combining said first diluent stream and said second diluent stream to form a third diluent stream; and
removing a representative preselected volume of fluid containing said sample material from said third diluent stream to provide a diluted sample.

12. A method in accordance with claim 11 wherein removing said representative preselected volume of fluid containing said sample material comprises removing said preselected volume of fluid containing sample material at a preselected location within said third diluent stream and at a preselected time following the injection of said sample material into said first diluent stream.

13. A method in accordance with claim 11 wherein said preselected time is within a period of time during which a representative, generally uniform concentration of said sample material is present at said preselected location within said third diluent stream.

14. A method in accordance with claim 4 wherein removing a representative preselected volume of fluid containing said sample material from said third diluent stream comprises injecting a preselected volume of fluid containing said sample material from said third diluent stream into the carrier fluid of a chromatographic carrier stream associated with a chromatographic separation means, and wherein said method additionally comprises passing said chromatographic carrier stream through a chromatographic separation column.

15. A method in accordance with claim 14 wherein said carrier fluid and said diluent fluid are of substantially the same composition.

16. A method in accordance with claim 15 additionally comprising using the effluent from said chromatographic carrier stream as at least a portion of the diluent material for said first and second diluent streams.

17. A method in accordance with claim 16 wherein removing said representative preselected volume of fluid containing said sample material comprises removing said preselected volume of fluid containing sample material at a preselected location within said third diluent stream and at a preselected time following the injection of said sample material into said first diluent stream.

18. A method in accordance with claim 17 wherein said preselected time is within a period of time during which a representative, generally uniform, concentration of said sample material is present at said preselected location within said third diluent stream.

19. A method in accordance with claim 18 additionally comprising filtering the material flowing through said third diluent stream upstream of said preselected location within said third diluent stream.

20. A method in accordance with claim 16 wherein removing said representative preselected volume of fluid containing said sample material comprises detecting the presence of sample material at a first preselected location within said third diluent stream and removing said preselected volume of fluid containing sample material at a second preselected location within said third diluent stream downstream of said first preselected location in predetermined time relationship with the detection of the presence of sample material at said first predetermined location.

21. A method in accordance with claim 16 further comprising increasing the flow rate of said first diluent stream after said representative preselected volume of fluid containing sample material is removed from said third diluent stream.

22. A method in accordance with claim 11 wherein removing said representative preselected volume of fluid containing said sample material comprises detecting the presence of sample material at a first preselected location within said third diluent stream and removing said preselected volume of fluid containing sample material at second preselected location within said third diluent stream downstream of said first preselected location in predetermined time relationship with the detection of the presence of sample material at said first predetermined location.

23. A method in accordance with claim 11 further comprising increasing the flow rate of said first diluent stream after said representative preselected volume of fluid containing sample material is removed from said third diluent stream.

* * * * *